US006743447B2

(12) United States Patent
Labergerie et al.

(10) Patent No.: US 6,743,447 B2
(45) Date of Patent: Jun. 1, 2004

(54) PULVERULENT MANNITOL AND PROCESS FOR PREPARING IT

(75) Inventors: Erik Labergerie, Lestrem (FR); Philippe Lefevre, Merville (FR); José Lis, La Gorgue (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/819,496

(22) Filed: Mar. 28, 2001

(65) Prior Publication Data

US 2003/0026832 A1 Feb. 6, 2003

(30) Foreign Application Priority Data

Mar. 29, 2000 (FR) .............................................. 00 03954

(51) Int. Cl.$^7$ ................................................. A61K 9/14
(52) U.S. Cl. ....................................................... 424/489
(58) Field of Search ................ 424/489, 499, 424/490

(56) References Cited

U.S. PATENT DOCUMENTS 3,145,146 A     8/1964   Lieberman et al.
3,341,415 A     9/1967   Scott
4,661,647 A     4/1987   Serpelloni et al.
5,573,777 A   * 11/1996   Serpelloni et al. .......... 424/440

FOREIGN PATENT DOCUMENTS

JP    61-085330    10/1984

* cited by examiner

*Primary Examiner*—Thurman K. Page
*Assistant Examiner*—Robert M. Joynes
(74) *Attorney, Agent, or Firm*—Sturm & Fix LLP

(57) ABSTRACT

The present invention concerns pulverulent mannitol characterized in that it has an average diameter of between 60 and 200 $\mu$m, preferably of between 80 and 180 $\mu$m, a packed density, determined according to a Test A, of between 0.65 and 0.85 g/ml, preferably of between 0.7 and 0.8 g/ml and a flow factor of at least 60, preferably of between 60 and 90a process for obtaining and using the said pulverulent mannitol as an excipient in preparations intended in particular for the pharmaceutical field, and especially as a powder for filling hard capsules.

7 Claims, No Drawings

PULVERULENT MANNITOL AND PROCESS FOR PREPARING IT

The aim of the present invention is a pulverulent mannitol with a fine particle size, high density and excellent flow capability, and also having a high mannitol content and rapid rate of dissolution In water.

The invention also concerns a process for manufacturing the said mannitol as well as its use in the fields of pharmaceuticals and foodstuffs.

The pharmaceutical and foodstuffs industries consume large amounts of pulverulent polyols as excipients, bulk sweeteners or as carriers for additives. More precisely this involves sorbitol, xylitol, mannitol and maltitol.

Sorbitol has the advantage of being the least expensive product among these three polyols, which explains the fact that it is used very often. Nevertheless, as soon as any re-uptake of water has occurred, its high hygroscopicity leads to a product whose flow is difficult or even impossible.

To avoid this problem, a sorbitol with a coarser particle size is chosen, but then the time taken to dissolve in water generally becomes excessively long. In addition, the highly hygroscopic nature of sorbitol renders any use of this polyol out of the question when it is associated with active principles or ingredients that are very sensitive to water.

With regard to xylitol, this is scarcely ever used as an excipient because it has the disadvantage of caking under conditions of normal humidity, and does so even more readily than sorbitol.

Because of its low hygroscopicity, mannitol could be an excellent excipient since it is compatible with the majority of active ingredients, but unfortunately the product obtained by crystallisation in water beginning with a supersaturated solution has mediocre flow properties.

In fact, crystalline mannitol is excessively friable, leading to the formation of fine particles that are particularly detrimental to its flow properties.

In addition, because of its compact crystal structure, mannitol obtained by crystallisation in water has a poor ability to dissolve. This slow dissolution rate, although it can be an advantage in certain special applications, is always considered to be a major disadvantage in the cases that are of interest here, which hinders its use.

Other pulverulent forms of mannitol together with the means for obtaining the latter are described in the literature.

For example U.S. Pat. No. 3,341,415 deals with a method for preparing a pharmaceutical excipient containing at least 20% by weight of mannitol and an additional sugar chosen from among lactose, saccharose, erythritol, galactose and sorbitol. However, the process described is very tricky to operate on an industrial scale. Moreover, the product obtained is highly hygroscopic, very compact and very difficult to dissolve in water.

The patent application JP 61.85330 relates to a process for preparing excipients characterized by the fact that it consists of drying D-mannitol by spray atomization. However, it appears that the products obtained in this way contain more than 50% of particles smaller than 75 $\mu$m, which is detrimental to the correct flow of the product.

U.S. Pat. No. 3,145,146 describes a process for modifying the physical properties of mannitol by spray-drying, and the product thus obtained.

A powder whose particle size lies between 5 and 100 $\mu$m is obtained. However, this process consists of adding a binder, which can be a paraffin, a gum or a cellulose derivative, before the spray-atomization stage. In addition, at least 50% of the powder particles still have a size smaller than 75 $\mu$m, which is far from being ideal to obtain good flow.

All of the above shows that there is an unsatisfied need to have available a mannitol for use as an excipient that has a fine particle size, a high density and an excellent flow ability, it being advantageous for these properties to be combined with a high mannitol content and a rapid rate of dissolution in water.

Furthermore, in order for this excipient to be preferred for use as a powder to fill hard capsules, it has been found that it is necessary to have a product that will be compatible with the active ingredient with which it is associated, and that its free-flowing properties, homogeneity of mixing, dissolution profile and packed density conform to the required application.

To obtain an excipient of this kind having all the functional properties listed above, the applicant company has discovered that, contrary to all expectation, it is advisable to choose from among the polyols a pure crystalline mannitol and to modify its physical properties by using a suitable process such that it has at the same time a fine particle size, a high density and excellent flow capability, and in addition a high mannitol content and a rapid speed of dissolution in water.

Thus the applicant company has distinguished itself by reconciling all of these aims that were up to this time supposed to be irreconcilable, by devising and developing, through numerous investigations, a novel pulverulent mannitol.

Thus the invention relates to a pulverulent mannitol characterized in that it has:
- an average diameter of between 60 and 200 $\mu$m, preferably being between 80 and 180 $\mu$m,
- a packed density, determined according to a Test A, of between 0.65 and 0.85 g/ml, preferably between 0.7 and 0.8 g/ml,
- a flow factor of at least 60, preferably between 60 and 90.

The pulverulent mannitol according to the invention has an average diameter of between 60 and 200 $\mu$m, preferably between 80 and 180 $\mu$m. These values are determined on a COULTER® LASER LS granulometer by determining the volume size distribution of the particles of pulverulent mannitol.

Thus the size of the component particles of the pulverulent mannitol according to the invention enables it to maintain an average diameter relative to that of the majority of active ingredients and thus to obtain homogeneous mixtures of active ingredients with mannitol by granulometric (particle size) equivalence.

In fact, it has been found quite generally that an elevated active ingredient crystal size impairs their dissolution speed. Therefore an average diameter of between 80 and 200 $\mu$m is recommended.

The pulverulent mannitol according to the invention can also be characterized by its packed density.

The determination of the packed density is carried out according to the method specified in the operating instructions for the HOSOKAWA P.T.N. powder tester.

Under these conditions, the pulverulent mannitol according to the invention has a high packed density, i.e. comprised between 0.65 and 0.85 g/ml, and preferably comprised between 0.7 and 0.8 g/ml.

This high density value gives the pulverulent mannitol according to the invention properties that are particularly appropriate to its use as a filling agent for small hard capsules in pharmacology, namely a size that is more acceptable by patients.

In addition, the pulverulent mannitol according to the invention can also be characterized by its flowability, this property being especially appropriate when the said mannitol is used to fill hard capsules.

The ability of the said mannitol to flow is measured using the POWDER TESTER instrument marketed by the HOSOKAWA Company. This equipment enables the ability of a powder to flow to be measured under standardised, reproducible conditions and the calculation of a flow factor, also called the Carr Index.

The pulverulent mannitol according to the invention has an excellent flow factor, generally at least 60 and preferably of between 60 and 90.

This value is generally much better than that of the crystalline mannitol powders of the prior art, and is equivalent to mannitol powders obtained by extrusion or atomisation processes.

However, the products obtained by extrusion usually have a large particle size with an average diameter of between 250 and 600 $\mu$m, and those obtained by atomisation typically have a low packed density, less than 0.6 g/ml, which makes these two categories of product particularly poorly suited to the required areas of application.

The pulverulent mannitol according to the invention is characterised in that it also has a mannitol content at least equal to 96% by weight, preferably at least equal to 98% by weight.

Thus from the point of view of its chemical composition, the pulverulent mannitol according to the invention is relatively pure.

Thus it is surprising and unexpected that a pulverulent mannitol that already has such an ability to flow with a fine particle size and such a packed density simultaneously has such a high chemical purity.

In fact, as far as the applicant company knows, the only pulverulent mannitols that have good flowability comprise, as mentioned above, binders such as paraffin, gums or cellulose derivatives.

Finally, the pulverulent mannitol according to the invention is characterised by its rapid rate of dissolution in water, this rate being measured according to Test B developed by the applicant company.

To measure the speed of dissolution in water according to Test B, exactly 5 g of the product to be tested is put into 150 ml of deionised, degassed water maintained at 20° C. and stirred at the rate of 200 rpm.

The dissolution speed corresponds to the time needed, after introducing the product, to visually obtain perfect clarity of the suspension prepared in this way.

Under these conditions the pulverulent mannitol according to the invention has a rapid dissolution rate, i.e. of between 20 and 60 seconds. These dissolution rates are generally well suited to the intended applications.

The pulverulent mannitol according to the invention can be obtained by carrying out a mannitol powder granulation step by a wet method using a binder, followed by a maturing stage by drying the pulverulent mannitol thus obtained.

To obtain a pulverulent mannitol according to the invention and having the stated functional characteristics, the applicant company has discovered that it is appropriate to choose as a starting material mannitol a mannitol powder that can be obtained by crystallisation in water or in some other solvent such as alcohol.

The particle size of the said mannitol powder starting material does not in itself constitute a limiting factor for the production of a pulverulent mannitol according to the invention.

With regard to the binder, this consists of water or a mannitol syrup with a dry material content equal to at most 50% and preferably of between 20 and 40%, or even water vapour (steam) as will be exemplified below.

In a surprising and unexpected way, the applicant company has discovered that the granulation of a mannitol powder by a wet method using a binder enables the preparation in high yield of a product in accordance with the invention as far as its particle size, density and flowability are concerned.

In fact, the processes described in the past do not allow the totality of the desired characteristics to be obtained.

To carry out the granulation, it is possible to use for example a continuous mixer-granulator of the vertical FLEXOMIX type marketed by the HOSOKAWA SCHUGI company or the horizontal CB type marketed by the LÖDIGE company, into which the mannitol powder starting material to be granulated is introduced continuously via a weight dispensing device, and into which the binder (water, water vapour (steam) or the mannitol solution) is introduced continuously via a volumetric dispensing device. The granulation can also be carried out in a spray atomising tower or in a fluidised bed granulator.

Preferably a continuous mixer-granulator of the vertical HOSOKAWA SCHUGI FLEXOMIX type is chosen for use. The mannitol powder starting material and the binder are mixed very intimately in the mixer-granulator which is equipped with a shaft with knives arranged as blades and a system for atomising liquids by injection nozzles.

In a preferred mode of the process, good dispersion of the constituents and the agglomeration of the particles of mannitol powder starting material are achieved by mixing at high speed, i.e. at a value equal to at least 2000 rpm, preferably equal to at lease 3000 rpm. At the outlet of the mixer-granulator, the granules formed are discharged continuously onto a dryer. The discharge preferably takes place by gravity in the case of the said vertical granulator, and by thrust, via the shaft of the rotating knives if the horizontal granulator is used.

This second stage of drying at the outlet of the mixer-granulator enables the water originating from the binder to be removed and the crystallisation of the dry material originating from the binder in the case where a mannitol solution was used, in such a way that the crystallisation takes place after the foregoing granulation stage. The dryer can be, for example, a fluidised bed dryer or a rotary maturing drum.

The pulverulent mannitol according to the invention is obtained after cooling and optionally sieving. In this case, the fine particles can be recycled directly to the start of the granulation, and the coarse particles can be crushed/ground and recycled to the input of the screening or to the input of the granulation.

Other characteristic features and advantages of the invention will be apparent on reading the following Examples. However, they are given here only as an illustration and are not limiting.

EXAMPLE 1

A vertical SCHUGI FLEXOMIX mixer-granulator is fed continuously via a powder dispenser at a feedrate of 500 kg/hr with a crystalline mannitol manufactured by crystallisation.

The mixer-granulator is also fed continuously with a mannitol solution containing 50% by weight at 80° C. and at a feedrate of 60 to 70 l/hr via an atomization nozzle. The rotating knife shaft is previously adjusted to a speed of 3000 rpm.

The moist granulated powder at the outlet of the mixer-granulator falls continuously under gravity into a SCHUGI fluidised bed dryer-maturer with 4 compartments. In the first 3 compartments the granulated product is dried by air at 125–150° C. and is then cooled by air at 30° C. in the last compartment.

The granulated, dried and cooled product is then sieved continuously on a rotary screen fitted with a 740 μm metallic cloth.

The crystalline mannitol starting material A and the pulverulent mannitol B according to the invention, prepared using mannitol solution as binder, have the characteristic properties listed in Table I below.

TABLE I

| Parameters | A | B |
| --- | --- | --- |
| Average laser diameter (μm) | 62 | 106 |
| Packed density (g/ml) | 0.79 | 0.71 |
| Flow factor (value/100) | 40 | 67 |
| Mannitol content (% wt./wt.) | >98 | >98 |
| Rate of dissolution in water (s) | 83 | 36 |

EXAMPLE 2

A vertical SCHUGI FLEXOMIX mixer-granulator is fed continuously via a powder dispenser at a feedrate of 500 kg/hr with a crystalline mannitol manufactured by crystallisation.

The mixer-granulator is also fed continuously with a mannitol solution containing 40% by weight at 90° C. and at a feedrate of 90 1/hr via an atomization nozzle. The rotating knife shaft is previously adjusted to a speed of 3000 rpm.

The moist granulated powder at the outlet of the mixer-granulator falls continuously under gravity into a SCHUGI fluidised bed dryer-ripener with 4 compartments. In the first 3 compartments the granulated product is dried by air at 125–150° C. and is then cooled by air at 30° C. in the last compartment.

The granulated, dried and cooled product is then sieved continuously on a rotary screen fitted with a 740 μm metallic cloth.

The crystalline mannitol starting material A and the pulverulent mannitol C according to the invention, prepared using mannitol solution as binder, have the characteristic properties listed in Table II below.

TABLE II

| Parameters | A | C |
| --- | --- | --- |
| Average laser diameter (μm) | 62 | 126 |
| Packed density (g/ml) | 0.79 | 0.71 |
| Flow factor (value/100) | 40 | 65 |
| Mannitol content (% wt./wt.) | >98 | >98 |
| Speed of dissolution in water (s) | 82 | 43 |

EXAMPLE 3

A vertical SCHUGI FLEXOMIX mixer-granulator is fed continuously via a powder dispenser at a feedrate of 450 kg/hr with a crystalline mannitol manufactured by crystallisation.

The mixer-granulator is also fed continuously with steam at a pressure of 1.3 bar and a temperature of 107° C. and at a feedrate of 40 kg/hr via an atomization nozzle. The rotating knife shaft is previously adjusted to a speed of 3000 rpm.

The moist granulated powder at the outlet of the mixer-granulator falls continuously under gravity into a SCHUGI fluidised bed dryer-maturer with 4 compartments. In the first 3 compartments the granulated product is dried by air at 150° C. and is then cooled by air at 30° C. in the last compartment.

The granulated, dried and cooled produce is then sieved continuously on a rotary screen fitted with a 740 μm metallic cloth.

The crystalline mannitol starting material A and the pulverulent mannitol D according to the invention, prepared using steam as binder, have the characteristic properties listed in Table III below.

TABLE III

| Parameters | A | D |
| --- | --- | --- |
| Average laser diameter (μm) | 62 | 101 |
| Packed density (g/ml) | 0.79 | 0.70 |
| Flow factor (value/100) | 40 | 67 |
| Mannitol content (% wt./wt.) | >98 | >98 |
| Speed of dissolution in water (s) | 83 | 33 |

EXAMPLE 4

A vertical SCHUGI FLEXOMIX mixer-granulator is fed continuously via a powder dispenser at a feedrate of 800 kg/hr with a crystalline mannitol manufactured by crystallisation.

The mixer-granulator is also fed continuously with a mannitol solution containing 20% by weight at a temperature of 50° C. and at a feedrate of 75 1/hr via an atomization nozzle. The rotating knife shaft is previously adjusted to a speed of 3650 rpm.

The moist granulated powder at the outlet of the mixer-granulator falls continuously under gravity into a SCHUGI fluidised bed dryer-maturer with 4 compartments. In the first 3 compartments the granulated product is dried by air at 120–125° C. and is then cooled by air at 25° C. in the last compartment.

The granulated, dried and cooled product is then sieved continuously on a rotary screen fitted with a 740 μm metallic cloth.

The crystalline mannitol starting material E and the pulverulent mannitol F according to the invention, prepared using mannitol solution as binder, have the characteristic properties listed in Table IV below.

TABLE IV

| Parameters | E | F |
| --- | --- | --- |
| Average laser diameter (μm) | 90 | 101 |
| Packed density (g/ml) | 0.76 | 0.77 |
| Flow facter (value/100) | 40 | 60 |
| Mannitol content (% wt./wt.) | >98 | >98 |
| Speed of dissolution in water (s) | 47 | 52 |

EXAMPLE 5

Other pulverulent products according to the invention are prepared by applying the process described in Example 1 but modifying the operating conditions so as to obtain a range of samples having a varying particle size, packed density and flowability. The products obtained have the characteristic properties shown in Table V below, and are compared to pulverulent mannitols otherwise known.

TABLE V

| Parameters | Products according to the invention | Products produced by crystallisation | Products produced by extrusion | Products produced by atomisation |
|---|---|---|---|---|
| Average laser diameter ($\mu$m) | 100–200 | 50–150 | 230–800 | 80–200 |
| Packed density (g/ml) | 0.7–0.8 | 0.75–0.8 | 0.65–0.75 | <0.6 |
| Flow factor (value/100) | 60–90 | <60 | 60–80 | 70–90 |
| Mannitol content (% wt./wt.) | >98% | >98% | >98% | >98% |
| Speed of dissolution in water (s) | 20–60 | 15–25 | 60–80 | 8–15 |

Compared to products of the prior art, the pulverulent mannitols according to the invention all have excellent functional properties, flowability and rate of dissolving in water with a fine particle size and high packed density, and at the same time a high mannitol content. These new products, particularly those with a high flowability with a packed density greater than 0.7 g/ml, are especially suitable for problem-free use in the pharmaceutical industries, in particular as excipients for use in filling hard capsules. As far as the applicant company knows, pulverulent mannitol having such properties does not exist.

EXAMPLE 6

A comparison was made between the pharmaceutical properties of pulverulent mannitol according to the invention (in the form of the pulverulent mannitol B of Example 1) and the prior art. The pharmacotechnical properties were measured using the methods of the European Pharmacopoeia and shown in Table VI below. The particle sizes were determined by laser granulometry.

TABLE VI

| | Products produced by crystallisation | Products produced by atomisation | Products produced by extrusion | Pulverulent mannitol B |
|---|---|---|---|---|
| Apparent volume (ml) | | | | |
| Before packing | 162 | 208 | 152 | 182 |
| $V_0$ | 156 | 206 | 148 | 167 |
| After packing | 126 | 188 | 136 | 143 |
| $V_{10}$ | 124 | 186 | 135 | 142 |
| $V_{500}$ | | | | |
| $V_{1250}$ | | | | |
| Packing ability $V_{10}$-$V_{500}$ (ml) | 30 | 18 | 12 | 24 |
| Apparent volumetric mass (g/ml) | | | | |
| Before packing | 0.617 | 0.481 | 0.658 | 0.549 |
| After packing | 0.806 | 0.538 | 0.741 | 0.704 |
| Flowing (s) | Infinite | 7 | 9 | 5 |
| Particle size ($\mu$m) | 80 | 170 | 400 | 106 |

The pulverulent mannitol B according to the invention has Theological properties that are indispensable and sought after in numerous pharmaceutical formulation processes, i.e.:

free flowability, enabling uniformity of the weight of the medication and dosage of the active ingredient, high free and packed densities, enabling the size of the final medication to be reduced, consequently making it easier to swallow, a particle size compatible with chose of the majority of active ingredients, which ensures homogeneity of distribution of the active ingredient and a precise dosage of the active ingredient in the medication.

On the contrary, it is found that crystallised mannitol does not flow freely, and its use necessitates a prior granulation stage.

Mannitol powder originating from the atomisation process has lower free and packed densities, which leads to less compacting in the medicinal processes and to medications with larger dimensions and thus more difficult to swallow.

Finally, mannitol powder produced by extrusion has a particle size that is too large relative to that of the active ingredients; nevertheless it will be used in formulations where the active ingredient is granulated or coated.

EXAMPLE 7

A comparison was made between a pulverulent mannitol according to the invention (in the form of the pulverulent mannitol B of Example 1) and other mannitol powders in the formulation of a powder for filling hard capsules.

The hard capsule envelope is Size 2, a small size that is easy to swallow, and the weight of powder is 250 mg per hard capsule.

The filling of the hard capsules is semi-automatic, by levelling and vibration.

For this application, the required pharmacotechnical properties are usually:

free flowability, for uniform filling of the hard capsule, a packed density greater than 0.675 g/ml, enabling the inclusion of 250 mg of powder in the Size 2 hard capsule (internal volume 0.37 ml)

a particle size of between 80 and 150 $\mu$m to obtain homogeneous mixing with the active ingredient.

Table VII below shows a comparison of the required pharmacotechnical properties.

TABLE VII

| Required properties | Test performed | Products produced by crystallisation | Products produced by atomisation | Products produced by extrusion | Pulverulent mannitol B |
|---|---|---|---|---|---|
| Free flowability | Flowability (s) | Infinite | 7 | 9 | 5 |
| Packed density (>0.675) | Apparent volumetric mass after packing $V_{1250}$ g/ml | 0.806 | 0.538 | 0.741 | 0.704 |
| Particle size (80–150 $\mu$m) | Average laser diameter ($\mu$m) | 80 | 170 | 400 | 106 |

The pulverulent mannitol B according to the invention is the only one having all of the required properties, and is thus the only one that allows the formulation of this powder for gelatine capsules.

EXAMPLE 8

A comparison was made between a pulverulent mannitol according to the invention (in the form of the pulverulent mannitol B of Example 1) and other mannitol powders in the formulation of a powder for filling hard capsules.

The hard capsule envelope is Size 0, a size allowing a high dosage of active ingredients, i.e. up to 700 mg.

The hard capsules are filled by the compression metering technique.

To formulate the powder for filling the hard capsules, filling is simulated on a specially designed apparatus equipped with a die having a volume of 0.78 ml and a punch with a diameter of 6.3 mm.

The lower part of the die can be opened, thus allowing the ejection of the slug formed in a Size 0 hard capsule envelope.

During the test, the powder is compressed into the die using the punch until a slug that is sufficiently coherent to enable it to be handled is obtained.

It is necessary to avoid this slug having excessive cohesion, which would reduce the speed of dissolution, because rapid dissolving is necessary in order for the medication to have an immediate therapeutic effect.

A lubricant, magnesium stearate, is added to the powder to make it easier for the slug to slide as it is being ejected.

Its content depends on the powder used, and is determined empirically.

To choose the pulverulent mannitol that is best suited to this formulation of powder for hard capsules, experiments were carried out with binary (two-component) mixtures of pulverulent mannitol and magnesium stearate.

Table VIII below shows all of the results obtained.

TABLE VIII

|  | Products produced by crystallisation | Products produced by atomisation | Products produced by extrusion | F |
|---|---|---|---|---|
| Amount of magnesium stearate (%) | 0.9 | 1.4 | 0.9 | 1 |
| Initial density of the powder (g/ml) | 0.67 | 0.49 | 0.68 | 0.63 |
| Final density of the slug (g/ml) | 0.99 | 0.84 | 1.05 | 1.09 |
| Weight of the slug (mg) | 520 | 390 | 530 | 494 |
| Size of the slug (mm) | 16.89 | 14.85 | 16.12 | 14.48 |
| Dissolution time of the hard capsule (s) | 60 | 165 | 430 | 180 |
| Maximum quantity in a Size 0 capsule (mg) | 671 | 572 | 717 | 744 |

The most suitable pulverulent mannitol is the mannitol according to the invention, based on the criteria with regard to:

uniform filling of the slug during the experiments, high final density, greater than all of the other pulverulent mannitols, short dissolution time (3 minutes)

In fact the crystallised mannitol caused problems of fluctuation of the weight of the slug due to its lack of flowability.

The mannitol produced by atomisation gave slugs whose density was too low; by replacing it with the pulverulent mannitol of the invention it is possible to reduce the size of the hard capsule, which considerably improves patient comfort.

Mannitol manufactured by extrusion has an unsuitable particle size. Apart from the fact that the difference between it and the active ingredient causes problems wish uneven dosage, it also results in a hard capsule dissolution rate that is too slow.

The pulverulent mannitol according to the invention is the only one that allows the formulation of powder for filling hard capsules in conformity with all of the defined criteria.

What is claimed is:

1. A pulverulent mannitol having:

an average diameter of between 80 and 180 $\mu$m;

a packed bulk density, determined according to the method specified in the operating instructions for the HOSOKAWA P.T.N powder tester, of between 0.70 and 0.80 g/ml;

a flow factor of at least 60.

2. The pulverulent mannitol according to claim 1 having:

a flow factor of between 60 and 90.

3. The pulverulent mannitol according to claim 1, having a mannitol content at least equal to 96% by weight.

4. The pulverulent mannitol according to claim 3, having a mannitol content at least equal to 98% by weight.

5. The pulverulent mannitol according to claim 1, having a rate of dissolution of between 20 and 60 seconds when dissolving 5 g of the product until perfect visual clarity, into 150 ml of deionised, degassed water maintained at 20° C. and stirred at 200 rpm.

6. A process for preparing a pulverulent mannitol having the characteristics of the pulverulent mannitol according to claim 1, comprising a step of granulating a crystalline mannitol powder by a wet route with the aid of a binder, and a maturing step, by drying, of the pulverulent mannitol thus obtained.

7. The preparation process according to claim 6, wherein the granulation stage is carried out in a continuous mixer granulator.

* * * * *